(12) United States Patent
Ladebeck et al.

(10) Patent No.: US 8,805,474 B2
(45) Date of Patent: Aug. 12, 2014

(54) METHOD FOR RECORDING AND EVALUATING PET DATA RECORDED AT THE SAME TIME AS MAGNETIC RESONANCE DATA USING A COMBINED MAGNETIC RESONANCE/PET APPARATUS, AND A COMBINED MAGNETIC RESONANCE/PET APPARATUS

(75) Inventors: Ralf Ladebeck, Erlangen (DE); Sebastian Schmidt, Weisendorf (DE)

(73) Assignee: Siemens Aktiengesellschaft, Munich (DE)

( * ) Notice: Subject to any disclaimer, the term of this patent is extended or adjusted under 35 U.S.C. 154(b) by 524 days.

(21) Appl. No.: 13/008,956

(22) Filed: Jan. 19, 2011

(65) Prior Publication Data
US 2011/0178387 A1 Jul. 21, 2011

(30) Foreign Application Priority Data
Jan. 21, 2010 (DE) .......................... 10 2010 005 287

(51) Int. Cl.
*A61B 5/05* (2006.01)
(52) U.S. Cl.
USPC ....................... 600/411; 250/363.09; 382/131
(58) Field of Classification Search
None
See application file for complete search history.

(56) References Cited

U.S. PATENT DOCUMENTS

| | | | |
|---|---|---|---|
| 7,323,874 B2 | 1/2008 | Krieg et al. | |
| 7,403,011 B2 | 7/2008 | Burdick, Jr. et al. | |
| 8,299,438 B2 * | 10/2012 | Fenchel et al. | 250/363.09 |
| 2008/0027308 A1 | 1/2008 | Ladebeck | |
| 2008/0312526 A1 * | 12/2008 | Gagnon et al. | 600/411 |
| 2011/0123083 A1 * | 5/2011 | Ojha et al. | 382/131 |

FOREIGN PATENT DOCUMENTS

| | | |
|---|---|---|
| DE | 102007007623 A1 | 8/2007 |
| DE | 102006027417 A1 | 12/2007 |
| DE | 102005015071 A1 | 10/2008 |
| WO | WO 2008131459 A1 | 10/2008 |

* cited by examiner

*Primary Examiner* — Unsu Jung
*Assistant Examiner* — Saurel J Selkin
(74) *Attorney, Agent, or Firm* — Harness, Dickey & Pierce, P.L.C.

(57) ABSTRACT

A method is disclosed for recording and evaluating PET data recorded at the same time as magnetic resonance data using a combined magnetic resonance/PET apparatus, wherein in the context of a pulse sequence for recording the magnetic resonance data a magnetic resonance recording facility, including at least one gradient coil and at least one high-frequency coil, is activated. In at least one embodiment, the method includes recording the PET data and assigning the recorded PET data after the recording time point to at least two data groups assigned to a predetermined operating state of the magnetic resonance recording facility; for each data group, determining a measure of similarity of the PET data contained therein to the PET data as a whole and/or to PET data of at least one further data group, whereby if the measure of similarity is below a threshold value, the PET data of the data group is rejected and/or further evaluated separately.

17 Claims, 2 Drawing Sheets

METHOD FOR RECORDING AND EVALUATING PET DATA RECORDED AT THE SAME TIME AS MAGNETIC RESONANCE DATA USING A COMBINED MAGNETIC RESONANCE/PET APPARATUS, AND A COMBINED MAGNETIC RESONANCE/PET APPARATUS

PRIORITY STATEMENT

The present application hereby claims priority under 35 U.S.C. §119 on German patent application number DE 10 2010 005 287.6 filed Jan. 21, 2010, the entire contents of which are hereby incorporated herein by reference.

FIELD

At least one embodiment of the invention generally relates to a method for recording and evaluating PET data recorded at the same time as magnetic resonance data using a combined magnetic resonance/PET apparatus, wherein in the context of a pulse sequence for recording the magnetic resonance data a magnetic resonance recording facility, comprising at least one gradient coil and at least one high-frequency coil, is activated. At least one embodiment of the invention further generally relates to an associated combined magnetic resonance/PET apparatus.

BACKGROUND

It has been recognized for some time that a combination of the PET (Positron Emission Tomography) and magnet resonance image recording modalities is expedient due to the advantageously complementary data. Therefore combined magnetic resonance/PET apparatuses have been proposed, with which it is possible to record accordingly co-registered magnetic resonance data and PET data at the same time.

However the problem arises that the activity of the magnetic resonance recording facility in some instances produces unintended interference with receiving on the PET side. This is due in particular to the high-frequency radiation transmitted by the magnetic resonance system and the gradient activity of the magnetic resonance system, which produces temporary interference in the PET components located within the magnetic resonance system.

To resolve such problems it has been proposed that the magnetic resonance components and the PET components should be shielded from one another. Such proposals are disclosed for example in DE 10 2007 007 623 A1 and DE 10 2005 015 071 A1. However such shielding is not always completely successful, so that the underlying problems remain even when the measures described there are applied.

The situation is complicated in that many such interference instances only occur sporadically, for example in certain states of the system as a whole or very specific magnetic resonance pulse sequences, which contain particular series of gradients or high-frequency pulses. Since further influencing factors, for example temperature, can also play a role, it is practically impossible to test all the theoretically possible states of the system and exclude any mutual influences.

Mutual influences become particularly disadvantageous when the PET data is falsified as a result, which can mean that a false diagnosis or no diagnosis at all is produced in a medical situation.

SUMMARY

In at least one embodiment of the invention, a recording and evaluation method is specified, with which the influence of interference produced by the magnetic resonance recording on the evaluation process can be reduced or ideally completely avoided.

In at least one embodiment, the method includes:
recording the PET data and assigning the recorded PET data according to the recording time point to at least two data groups assigned to a predetermined operating state of the magnetic resonance recording facility,
for each data group determining a measure of similarity of the PET data contained therein to the PET data as a whole and/or to PET data of at least one further data group,
whereby if the measure of similarity is below a threshold value, the PET data of the data group is rejected and/or further evaluated separately.

At least one embodiment of the invention therefore utilizes the experience and knowledge that such interference is in most instances associated with certain operating states of the magnetic resonance recording facility, in order to assign the recorded PET data to different operating states with arbitrarily precise abstraction. This is possible, as the magnetic resonance sequences used are already known beforehand, in other words it is known at which time point which operating state of the magnetic resonance recording facility is present. Also in respect of the PET data the time point at which an event occurred is ultimately recorded for each event. It is thus possible to group the PET data by time and to determine in which operating state of the magnetic resonance recording facility it was recorded.

PET data assigned to identical operating states of the magnetic resonance recording facility therefore forms data groups. These data groups are then compared with all the recorded PET data or at least another data group to determine a measure of similarity. If there is interference with the PET data recording, a major deviation from the remaining data in the other operating states can be expected, so that if the measure of similarity is below a threshold value, it can be established with a high level of probability that there is interference with the PET data. The PET data in a data group deviating thus from the other PET data is removed during the course of the evaluation from the remainder of the data, in that it is either rejected as defective from the outset, or it is further evaluated separately, if for example correction is still conceivable or the interference is not serious enough to influence the further evaluation in a falsifying manner.

In other words in conditions where there is no interference the PET data should only show random scatter over time (noise), so that ultimately all the data groups should feature a very high level of correlation and should produce identical images to the PET data as a whole. This changes if for example PET data measured during the rising edge of a gradient is subject to interference, as in such an instance the data group subject to interference exhibits a very small measure of similarity, while all the other data groups exhibit a very high measure of similarity.

To summarize, at least one embodiment of the invention therefore makes it possible to establish PET interference produced by magnetic resonance by classifying the PET data according to operating states of the magnetic resonance recording facility determined by the pulse sequence and determining the similarity between the resulting data groups. It is thus possible advantageously to achieve automatic detection and optionally, as examined in more detail below, correction of PET interference produced by magnetic resonance.

Provision can be made for state classes assigned to certain operating states of the magnetic resonance recording facility to be defined, with a data group being assigned to each state class occurring in a pulse sequence. In this embodiment certain, in particular predefined, state classes are defined which correspond to certain operational attributes of the magnetic resonance recording facility, which can of course also occur a number of times during one or more pulse sequences. All the PET data recorded during an operating state of the magnetic resonance recording facility which corresponds to that of the state class is then assigned to a data group. In principle it is therefore possible to divide the PET data into time slices, each time slice corresponding to the operating state of a state class. The time slices belonging to the same state class are combined into a single data group, for which the measure of similarity is then determined.

The operating states taken into account can be the activity of the or one gradient coil, in particular rising and/or falling edges and/or a constant energization, and/or the or one high-frequency coil. It should be emphasized again here that the procedure can have any degree of precision or abstraction. For example rises and amplitudes or rise regions and amplitude regions can be differentiated for the gradients, although it is equally conceivable to consider all types of rising or falling edges of the gradient currents as a specific operating state. The operating states of further components of the magnetic resonance recording facility can also be taken into account. Examples of these are receive coils and electronic systems.

However when looking at state classes, it is important ultimately not to select too many state classes, as it can be advantageous to obtain a large quantity of data for a statistic relating to the state classes, as examined in more detail below.

Operating states preceding the current operating state can expediently also be taken into account when assigning to data groups and/or defining state classes. It is thus possible for example to treat a rising gradient edge after a falling gradient edge differently from a rising edge after an idle state of the gradient coil.

Deviations and therefore smaller measures of similarity can also occur when circumstances outside the operating state of the magnetic resonance recording facility are relevant, for example heartbeat and/or respiration of a patient. These are periodic changes, which in most instances could not however correlate with the pulse sequence and therefore average out over time so that interference with the recording is not incorrectly assumed. Problems can occur in any case in this respect, if the data groups are selected too specifically, in that only a small quantity of data, in some instances recorded during a different heart state, is contained therein but also—and this instance could be of greater practical relevance—if the pulse sequences are triggered by an event in the cardiac cycle or respiratory cycle. A correlation can then definitely occur between the pulse sequence and the heart beat or respiration.

It is possible to take into account the patient state for example by taking into account at least one further additional parameter, in particular one describing the patient state, when assigning the PET data to the data groups. The data groups and the division of the PET data as a whole are then no longer defined only on the basis of the operating states of the magnetic resonance recording facility but an additional parameter describing the patient state in particular is also used as a differentiating parameter. For example provision can be made for the PET data (and therefore also the data groups) to be assigned to the systole and diastole of the examined patient. Provision can be made here for only PET data with corresponding additional parameters to be taken into account when calculating the measure of similarity. Essentially therefore PET data recorded during the systole can only be compared with other PET data also recorded during the systole and diastolic PET data is likewise only compared with other diastolic PET data. With continuous additional parameters provision can of course also be made for intervals to be defined, within which a comparison is expedient. In the case of recordings on which patient states such as heartbeat and respiration have a greater influence or in the case of pulse sequences triggered by patient states, these embodiments advantageously allow influences of such patient states on the measure of similarity to be largely excluded. Nonetheless it should be noted that it is also within the scope of at least one embodiment of the inventive method specifically to wish to reject immediately interference/incorrect measurements produced by the patient state itself.

Measures of similarity are widely known within the context of statistical considerations. Ultimately any suitable measures of similarity can be used, for example measures of correlation or a chi square test. Provision can be made here for the measure of similarity to be determined for the raw data (known as list mode data) and/or the sinograms and/or reconstruction data records (in other words reconstructions of the data sub-records defined by the data groups).

As mentioned above when determining the measure of similarity it is possible to carry out a comparison with the PET data as a whole. However provision can also expediently be made for a data group corresponding to an inactive operating state of the magnetic resonance recording facility to be used as a further data group when determining the measure of similarity. A PET data recording takes a very long time compared with the magnetic resonance data recording, so broad time regions are present in which no component of the magnetic resonance recording facility is active—the magnetic resonance recording facility is in an inactive operating state. At such time the PET data can of course not be influenced by components of the magnetic resonance recording facility so it can be assumed that the data of the corresponding data group was recorded without interference. This is therefore ideal as a basis for comparison.

Provision can furthermore advantageously be made for the determination of the measure of similarity to take place during the recording of the PET data and in the case of a measure of similarity below the threshold value for at least one data group for the PET data recording to be extended correspondingly. The determination of the measure of similarity can take place for example during the PET data recording if an adequate data base is available; therefore for example where the quantity of data exceeds a certain value or a number of data groups exceeds a certain number. It can then be checked during the PET data recording whether interference has occurred during operating states and PET data has to be removed from the normal evaluation. However this means that ultimately less evaluatable PET data is available. This is not desirable, so provision can be made during ongoing PET data recording for the PET data recording to be extended by a time interval that corresponds to the recording time of the deviating data group. It can thus be ensured that a sufficient quantity of PET data is available in each instance.

As mentioned above, provision can be made for PET data of a data group that indicates interference with the data recording, in that the measure of similarity is too low, to be simply rejected. If however the effect producing the interference is known and can be corrected, a correction of the PET data of the deviating data group can take place in the context of the separate evaluation. It is however also conceivable that even if the nature of the effect itself is not known exactly, the data may still contain usable information. It is therefore possible alternatively or additionally in the context of the separate evaluation to provide for a reconstruction data record to be determined from the PET data of the deviating data group and be displayed to a user, in particular at the same time as a reconstruction data record of the remaining PET data. The user can then decide whether the PET data of the deviating data group should be rejected or if it should be reinserted into the remaining PET data. It is of course also conceivable for the user to wish to keep the deviating PET data and evaluate it separately.

In a particularly advantageous embodiment of the present invention provision can be made for information relating to deviating data groups, in particular the state class and/or the extent of the deviation, to be stored in a database. This makes it possible in a manner of speaking to track the operating states of the magnetic resonance recording facility in which interference with the PET recording operation occurred, so that this data can optionally be subjected at a later stage to a specific statistical analysis, to determine the circumstances in which errors occur and optionally to discover their cause. This can then also lead for example to the possibility of correcting this data in the context of the separate evaluation and reinserting it into the remaining PET data. It is also conceivable for further additional information to be stored in the database, in particular information describing ambient conditions, for example temperature. It therefore becomes clearer over time in which operating states, in particular in which state class, PET interference occurs. Provision can expediently be made for at least one operating state, in particular a state class, in which deviations result, to be determined by evaluating the information, with PET data recorded during this operating state being rejected. In this manner, at least one embodiment of the inventive method establishes the basis for a learn function, so that it can be determined for each individual combined magnetic resonance/PET apparatus for example when interference may occur. It is then possible to reject data immediately during certain operating states or state classes generally or just in a certain operating mode, for example a fast operating mode. In particular provision can then be made in such a fast operating mode for no further determination of measures of similarity to take place.

In a further embodiment of the present invention provision can be made if the measure of similarity is below the threshold value for a warning message to be output and/or after all the PET data has been recorded for a portion of PET data that does not result in the measure of similarity dropping below the threshold value to be displayed. The user is then informed precisely whether interference has occurred and in the second instance even of the portion of PET data affected. This information can then be taken into account for example in the context of the evaluation or provision can be made for preparing a further PET recording. If the PET recording is still running, the user can also prompt the extension of the PET data recording. Naturally further information can be collated and output in addition to the two items of information mentioned here.

As well as the method of at least one embodiment of the invention also relates to a combined magnetic resonance/PET apparatus having a control device embodied to implement at least one embodiment of the inventive method. All the embodiments relating to at least one embodiment of the inventive method can be applied correspondingly to at least one embodiment of the inventive apparatus.

With such an apparatus it is therefore possible, optionally even during data recording, to check whether interference with the PET data recording has been present and to remove this data from further consideration, thereby generally allowing a safer and more reliable evaluation of the PET data.

BRIEF DESCRIPTION OF THE DRAWINGS

Further advantages and details of the present invention will emerge from the example embodiments described in the following and with reference to the drawing, in which.

DETAILED DESCRIPTION OF THE EXAMPLE EMBODIMENTS

Figure 1:
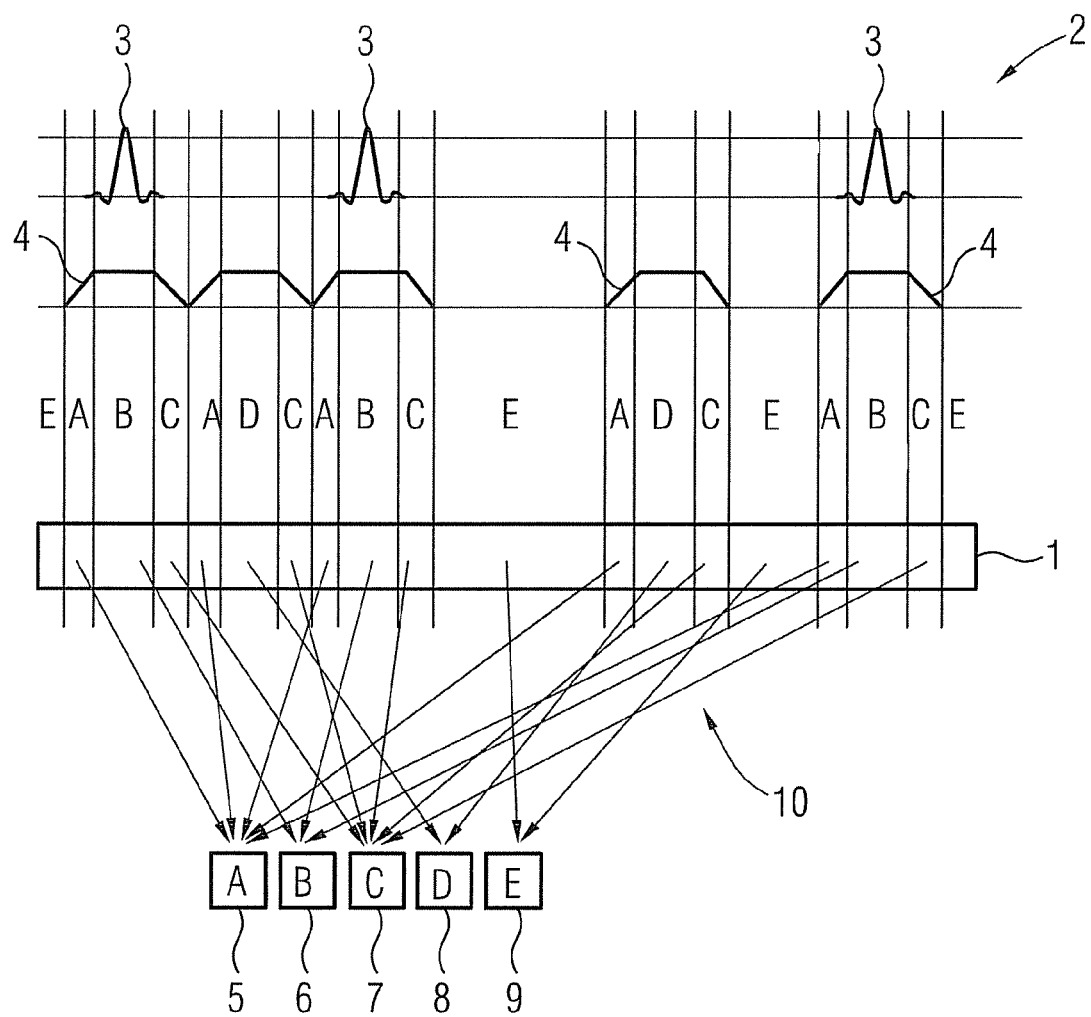
FIG. 1 shows a basic outline of the division of the PET data into data groups.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

An embodiment of the inventive method will first be described in more detail with reference to FIG. 1. Magnetic resonance data is recorded here at the same time as PET data 1 in a combined magnetic resonance/PET apparatus, to which end a magnetic resonance recording facility with three gradient coils and in this instance one high-frequency coil is activated. Activation takes place based on a pulse sequence 2 represented by the upper part of FIG. 1, with only the high-frequency pulses 3 and the gradient activity 4 being shown here. For a simpler illustration all the gradient coils here have been combined to form the gradient activities 4; it is of course also possible within the scope of an embodiment of the inventive method to consider each gradient coil per se.

The high-frequency pulses 3 and the gradient activity 4 ultimately define operating states of the magnetic resonance recording facility. Different operating states characterized by the pulse sequence 2 are combined here into state classes. In the rough classification undertaken by way of example in FIG. 1 there are ultimately five different state classes A-E. In the state class A a rising gradient edge is present, without a high-frequency pulse being output. The state class B is characterized by a constant gradient current, with a high-frequency pulse 3 being output at the same time. The state class C designates a rising edge of the gradient current without high-frequency pulse 3, the state class D a constant gradient current without simultaneous high-frequency pulse 3. Finally FIG. 2 shows the state class E, in which the magnetic resonance recording facility is inactive, which means that there is neither gradient activity 4 nor a high-frequency pulse 3 present.

It should be noted here that the classification into state classes can ultimately be undertaken with any degree of abstraction or precision. It is thus conceivable for example to differentiate according to the individual gradient coils or even to define intervals for the edge rises or the level of the constant current and thus to subdivide the state classes further. Further components of the magnetic resonance recording facility and its operating state can also be taken into account, for example receive coils and electronic systems. In particular it should be emphasized here however that it is also conceivable to take into account previous operating states when defining the state classes. It is thus possible for example for a rising edge that follows immediately after a falling edge to be assessed differently from a rising edge following an idle state. In this instance, as discussed in the example in FIG. 2, the second rise of the gradient current would have to be assigned to a different state class, for example a class A'.

It is therefore possible in this manner to subdivide the time series of the pulse sequence 2 into different time segments assigned to a state class, these thus being differentiated by the respective operating state of the magnetic resonance recording facility.

It should be noted here that it can be expedient in some instances also to use additional parameters, which may relate in particular to the state of the patient to be recorded. For example the state classes can be further subdivided according to whether a systolic or diastolic state is present. It is possible of course to undertake more exact classifications here, although it should be noted that in the further proceeding only PET data with comparable additional parameters can be compared.

After the corresponding time classification has been undertaken based on the pulse sequence 2, it is possible to assign the PET data 1 according to its recording time point in each instance to a data group 5-9. In this process all the PET data 1 recorded in the state class A is assigned to the group 5, all the PET data 1 recorded in the state class B is assigned to the data group 6, all the PET data 1 recorded in the state class C is assigned to the data group 7, all the PET data 1 recorded in the state class D is assigned to the data group 8 and all the PET data 1 recorded in the state class E is assigned to the data group 9. All the PET data 1 is therefore classified into data subrecords, specifically the data groups 5-9, as also shown visually by the arrows 10 in FIG. 2.

In other words the illustrated classification of the pulse sequence 2 causes the PET data 1 to be broken down into time slices, with time slices assigned to an identical or comparable operating state of the magnetic resonance recording facility then being combined again to form a data group 5-9.

In a next step of an embodiment of the inventive method provision is made to determine a measure of similarity in relation to a comparison data record for each data group 5-9. This comparison data record may be all the PET data 1 but in this exemplary embodiment provision is made for the data groups 5, 6, 7 and 8 respectively to be compared with the data group 9, which contains the PET data 1 recorded when the magnetic resonance recording system was inactive. It is therefore not possible for there to be any interference with the PET data recording produced by the magnetic resonance recording facility here.

The measure of similarity that can be based for example on a chi square test indicates how similar the compared PET data is, it being possible to compare the raw data, the sinograms and/or even already reconstructed reconstruction data records in this process. If the measure of similarity determined for a data group 5-9 is below a threshold value, it is assumed that there was, interference with the PET data recording in the corresponding operating state of the magnetic resonance recording facility.

This will be explained in more detail based on an example with reference to FIG. 2. FIG. 2 shows two graphs, the upper graph showing a gradient activity 11, the lower graph a PET signal 12. It can be seen that whenever a rising edge 13 of the gradient current is present, there is a clearly identifiable interference 14 in the PET signal 12.

Figure 2:
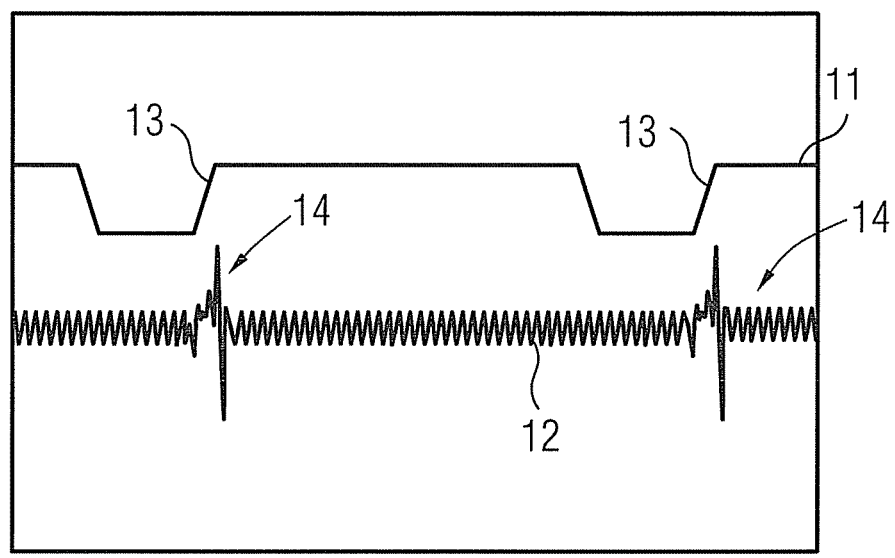
FIG. 2 shows a graph showing an example interference with the PET data recording and FIG. 3 shows an embodiment of an inventive combined magnetic resonance/PET facility.

This interference 14 therefore occurs in the state class A from FIG. 1. This means that a low value below the threshold value is found as the measure of similarity for the data group 5, while for the data groups 6, 7, 8 and 9 a high similarity value is displayed, which means that the data clearly correlates.

Once this has been determined the PET data of the data group 5 is removed from the further standard evaluation of the PET data 1. Provision can be made for it to be simply rejected but it is also conceivable for it to be subjected to a separate evaluation; for example if a correction is known, this correction is applied to it. Provision can however also be made for a specific reconstruction data record to be determined from the data of the data group 5 and for this to be displayed at the same time as the reconstruction data record determined from the remaining PET data of the data groups 6, 7, 8 and 9, so that a user can decide how to proceed with the data or whether it contains information that can still be evaluated or used.

In the example embodiment illustrated here, an embodiment of the inventive method is implemented while the PET data recording is still running, namely as soon as an adequate data base is available. Provision can then be made if a measure of similarity below the threshold value is present, to output a warning or the like, so that a user knows that some of his/her data will probably be unusable. However in each instance provision is made, as soon as a deviating data group is determined, in the example the data group 5, to extend the PET data recording automatically by the time for which the operating state of the magnetic resonance recording facility corresponds to the state class, in this instance state class A. This means that despite the loss of the data affected by interference, a sufficient quantity of evaluatable PET data 1 is available, in particular a quantity that is constant for every recording process.

It is expedient in each instance then to display for the user what portion of the PET data 1 has been determined as being affected by interference.

After every PET data recording information relating to deviating data groups found is stored in a database. In the present instance this comprises the state class and the extent of the deviation, optionally represented by way of the measure of similarity, although of course other information can also be stored in the database, in particular further general state information for the magnetic resonance/PET apparatus and its environment. One example of such additional information would be for example a measured temperature value, as it has proven that some instances of interference only occur below certain temperatures. In the present instance therefore the information that interference of a certain degree has occurred in the state class A would therefore be kept in the database.

The information in the database is now further evaluated to determine in which conditions and in which operating states interference with the PET measurement occurs. It is then possible in particular to use an operating mode in which the measure of similarity is no longer determined but PET data recorded in an operating state known for interference is immediately rejected and not used in the evaluation. Of course further information relating to circumstances can also be taken into account here, for example temperature information, if interference only takes place in a specific temperature range. It is thus possible with an embodiment of the inventive method to create a database over time, which can be used to identify states for the individual magnetic resonance/PET apparatus in which interference with the PET data recording takes place due to the magnetic resonance recording facility, specifically the pulse sequence 2 used.

Figure 3:
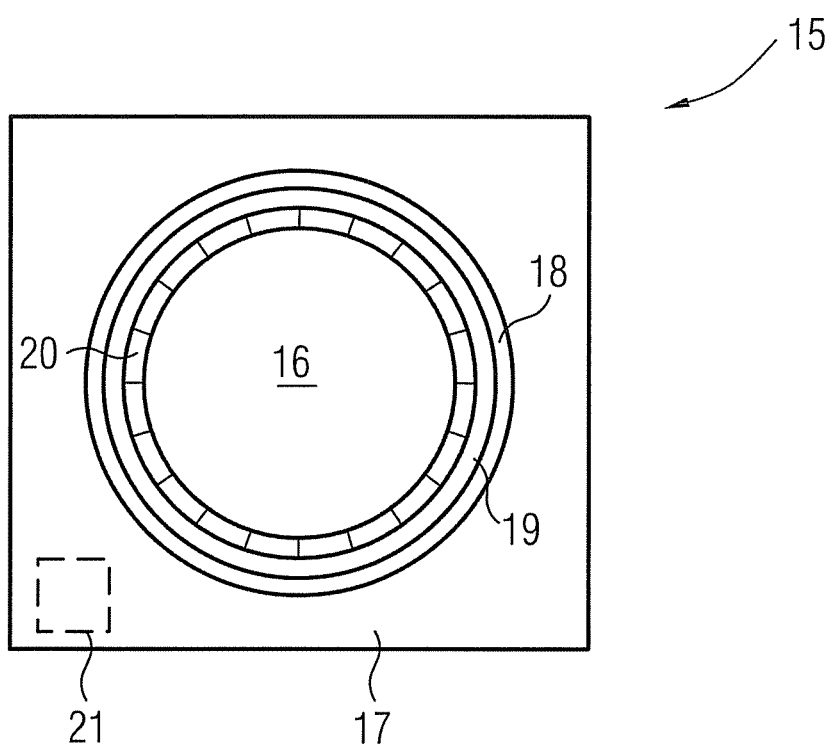

FIG. 3 finally shows a basic outline of an embodiment of an inventive combined magnetic resonance/PET apparatus 15. Disposed within a patient receiving space 16 of a basic magnet 17 first as parts of a magnetic resonance recording facility are a high-frequency coil 18 and a gradient coil 19. Inserted therein is also a PET detector ring 20. A control device 21 is also present to control the apparatus 15.

To determine the operating states of the magnetic resonance recording facility, in particular the gradient coil 19 and high-frequency coil 18, in which interference occurs with the PET data recording, the control device 21 is embodied to implement an embodiment of the inventive method, as described above.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of, the above-described and other example features of the present invention may be embodied in the form of an apparatus, method, system, computer program, non-transitory computer readable medium and non-transitory computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a non-transitory computer readable medium and is adapted to perform any one of the aforementioned methods when run on a computer device (a device including a processor). Thus, the non-transitory storage medium or non-transitory computer readable medium, is adapted to store information and is adapted to interact with a data processing facility or computer device to execute the program of any of the above mentioned embodiments and/or to perform the method of any of the above mentioned embodiments.

The non-transitory computer readable medium or non-transitory storage medium may be a built-in medium installed inside a computer device main body or a removable non-transitory medium arranged so that it can be separated from the computer device main body. Examples of the built-in non-transitory medium include, but are not limited to, rewriteable non-volatile memories, such as ROMs and flash memories, and hard disks. Examples of the removable non-transitory medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

| List of reference characters | |
|---|---|
| 1 | PET data |
| 2 | Pulse sequence |
| 3 | High-frequency pulse |
| 4 | Gradient activity |
| 5 | Data group |
| 6 | Data group |
| 7 | Data group |
| 8 | Data group |
| 9 | Data group |
| 10 | Arrow |
| 11 | Gradient activity |
| 12 | PET signal |
| 13 | Edge |
| 14 | Interference |
| 15 | Magnetic resonance/PET apparatus |
| 16 | Patient receiving space |
| 17 | Basic magnet |
| 18 | High-frequency coil |
| 19 | Gradient coil |
| 20 | PET detector ring |
| 21 | Control device |
| A | State class |
| B | State class |
| C | State class |
| D | State class |
| E | State class |

What is claimed is:

1. A method for recording and evaluating Positron Emission Tomography (PET) data recorded at the same time as magnetic resonance data using a combined magnetic resonance/PET apparatus, wherein in the context of a pulse sequence for recording the magnetic resonance data, a magnetic resonance recording device, including at least one gradient coil and at least one high-frequency coil, is activated, the method comprising:
    recording the PET data and assigning at least a first portion of the recorded PET data after the recording time point to at least two data groups assigned to an operating state of the magnetic resonance recording device;
    determining, for each of the at least two data groups, a measure of similarity of the PET data contained therein to at least one of the PET data and at least one further data group including a second portion of the PET data; and
    at least one of rejecting and further separately evaluating the PET data of each of the at least two data groups if the determined measure of similarity is below a threshold value.

2. The method as claimed in claim 1, wherein state classes, assigned to certain operating states of the magnetic resonance recording device, are defined, with a data group, of the at least two data groups, being assigned to each state class occurring in a pulse sequence.

3. The method as claimed in claim 2, wherein the operating states taken include the activity of at least one of the one gradient coil and the one high-frequency coil.

4. The method as claimed in claim 3, wherein activity of the at least one gradient coil includes at least one of rising and falling edges, and a constant energization.

5. The method as claimed in claim 1, wherein at least one further additional parameter is taken into account when assigning the at least the first portion of the PET data to the data groups.

6. The method as claimed in claim 5, wherein only PET data with corresponding additional parameters is taken into account when calculating the measure of similarity.

7. The method as claimed in claim 5, wherein the at least one further additional parameter includes a parameter describing the patient state.

8. The method as claimed in claim 1, wherein the measure of similarity is determined for at least one of raw data, sinograms and reconstruction data records.

9. The method as claimed in claim 1, wherein a data group corresponding to an inactive operating state of the magnetic resonance recording device is used as a further data group when determining the measure of similarity.

10. The method as claimed in claim 1, wherein the determination of the measure of similarity takes place during the recording of the PET data and in the case of a measure of similarity below the threshold value for at least one data group the PET data recording is extended correspondingly.

11. The method as claimed in claim 1, wherein, in the context of the separate evaluation, at least one of the PET data of the data group having similarity below the threshold value is corrected and a reconstruction data record is determined from the PET data of the data group having similarity below the threshold value and displayed to a user.

12. The method as claimed in claim 1, information relating to deviating data groups is stored in a database.

13. The method as claimed in claim 12, characterized in that at least one operating state, in particular a state class, in which deviations result, is determined by evaluating the information, with PET data recorded during this operating state being rejected.

14. The method as claimed in claim 12, wherein the information relating to data groups having similarity below the threshold value includes at least one of the state class and the extent of the deviation.

15. The method as claimed in claim 1, wherein, at least one of:
- if the measure of similarity is below the threshold value, a warning message is output, and
- after all the PET data has been recorded, a portion of PET data that does not result in the measure of similarity dropping below the threshold value is displayed.

16. The method as claimed in claim 1, wherein, in the context of the separate evaluation, at least one of the PET data of the data group having similarity below the threshold value is corrected and a reconstruction data record is determined from the PET data of the data group having similarity below the threshold value and displayed to a user, at the same time as a reconstruction data record of the remaining PET data.

17. A non-transitory computer readable medium including program segments for, when executed on a computer device, causing the computer device to implement the method of claim 1.

* * * * *